(12) United States Patent
Strickler et al.

(10) Patent No.: US 7,713,539 B2
(45) Date of Patent: May 11, 2010

(54) MEDICAL DEVICES CONTAINING RADIATION RESISTANT BLOCK COPOLYMER

(75) Inventors: Frederick H. Strickler, Natick, MA (US); Robert E. Richard, Wrentham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1695 days.

(21) Appl. No.: 10/894,400

(22) Filed: Jul. 19, 2004

(65) Prior Publication Data

US 2006/0013849 A1    Jan. 19, 2006

(51) Int. Cl.
  A61L 31/04    (2006.01)
  A61L 31/16    (2006.01)
  A61L 29/04    (2006.01)
  A61L 29/16    (2006.01)

(52) U.S. Cl. .................................................... 424/422

(58) Field of Classification Search ........................ None
See application file for complete search history.

(56) References Cited

U.S. PATENT DOCUMENTS

| | | | | |
|---|---|---|---|---|
| 4,250,611 A | * | 2/1981 | Wong | 29/460 |
| 4,824,675 A | * | 4/1989 | Wong et al. | 424/438 |
| 4,955,899 A | * | 9/1990 | Della Corna et al. | 623/1.46 |
| 5,395,869 A | * | 3/1995 | Kawamoto et al. | 524/108 |
| 5,468,803 A | * | 11/1995 | Takahashi et al. | 524/553 |
| 5,919,870 A | | 7/1999 | Letchford et al. | 525/333.2 |
| 6,486,278 B1 | | 11/2002 | Schiffino et al. | 526/160 |
| 6,545,097 B2 | | 4/2003 | Pinchuk et al. | 525/240 |
| 6,918,929 B2 | * | 7/2005 | Udipi et al. | 623/1.42 |
| 2002/0107330 A1 | | 8/2002 | Pinchuk et al. | 525/242 |
| 2004/0030062 A1 | * | 2/2004 | Mather et al. | 526/72 |
| 2004/0072950 A1 | * | 4/2004 | Machida et al. | 525/70 |
| 2006/0013849 A1 | * | 1/2006 | Strickler et al. | 424/422 |

FOREIGN PATENT DOCUMENTS

| | | |
|---|---|---|
| EP | 0401772 | 12/1990 |
| EP | 0478462 A1 | 4/1992 |
| JP | 60215036 | 10/1985 |
| WO | WO 2004/000380 A1 | 12/2003 |
| WO | WO 2005/011767 A1 | 2/2005 |
| WO | WO 2005/011772 A2 | 2/2005 |

OTHER PUBLICATIONS

Jeffrey Pyun et al., "Synthesis of Nanocomposite Organic/Inorganic Hybrid Materials Using Controlled/"Living" Radical Polymerization," *Chem. Mater.*, vol. 13, 2001, pp. 3436-3448.

Duck-Jei Park et al., "Synthesis and Properties of Maleic Anhydride-EPDM-Styrene Graft Terpolymer," *J. Macromol. Sci.—Pure Appl. Chem.*, vol. A32(7), 1995, pp. 1317-1328.

Thai Hoang et al., "Synthesis and Properties of Styrene-EPDM-Vinyl Acetate Graft Polymer," *Journal of Applied Polymer Science*, vol. 77, 2000, pp. 2296-2304.

Sung-Wook Han et al., "Synthesis and Photodegradable Properties of Methyl Vinyl Ketone-EPDM-Styrene Graft Terpolymer," *Journal of Applied Polymer Science*, vol. 67, 1998, pp. 1721-1727.

FMC Lithium Corporation, Polichelic™ Functional Polymers technical literature, 2001, 2 pp.

ExxonMobil Chemical, Vistalon™ EP(d)M—Polymer Variables, Sep. 1999, 1 p.

ExxonMobil Chemical, Vistalon™ EP(d)M Grades & Datasheets. http://www.exxonmobilchemical.com/Public_Products/EEB/EP_D_M/Worldwide/Grades and DataSheets. Jun. 9, 2003 download, 3 pp.

Joseph C. Salamone, ed., *Concise Polymeric Materials Encyclopedia*, CRC Press, Boca Raton, FL, 1999, pp. 812-814.

Karl J. Hemmerich, "Radiation Sterilization. Polymer Materials Selection for Radiation Sterilized Products," *Medical Device & Diagnostic Industry*, Feb. 2000. http://www.devicelink.com/mddi/archive/00/02/006.html.

Matyjaszewski, Krzysztof. "Well-Defined (Co)Polymers by Atom Transfer Radical Polymerization". Polymer Preprints. vol. 43. No. 2. p. 34-35. 2002.

Lutz, Jean-Francois; Matyjaszewski, Krzysztof. "Synthesis of Graft Terpolymers Poly (Alkyl Methacrylate)-G-Poly (D-Lactic Acid)/Poly (Dimethyl Siloxane) Using the Grafting Through Method in Atom Transfer Radical Polymerization". Polymer Preprints. vol. 43. No. 2. 2002. pp. 231-232.

Tsarevsky, Nicolay V.; Jia, Shijun; Tang, Chuanbing; Kowalewski, Tomasz; Matyjaszewski, Krysztof. "Synthesis of Block Copolymers of Acrylonitrile and N-Butyl Acrylate by Atom Transfer Radical Polymerization, Morphological Studies by Atomic Force Microscopy". Polymer Preprints. vol. 43. No. 2. 2002. pp. 207-208.

(Continued)

*Primary Examiner*—Robert A Wax
*Assistant Examiner*—Danah Al-Awadi
(74) *Attorney, Agent, or Firm*—Mayer & Williams PC; David B. Bonham; Keum J. Park

(57) ABSTRACT

The present invention relates generally to radiation-resistant medical devices which contain polymer regions for release of therapeutic agents. The present invention also relates to radiation-resistant block copolymer materials for use in connection with insertable or implantable medical devices. The radiation-sterilized medical device comprise (a) a release region and (b) at least one therapeutic agent and the release region comprises a radiation resistant copolymer that includes (i) a low $T_g$ hydrocarbon polymer block and (ii) one or more high $T_g$ polymer blocks.

32 Claims, 9 Drawing Sheets

OTHER PUBLICATIONS

Matyjaszewski, Krzysztof; Shipp, Devon A.; McMurtry, Gabriel P.; Gaynor, Scott G.; Pakula, Tadeusz. "Simple and Effective One-Pot Synthesis of (Meth) Acrylic Block Copolymers Through Atom Transfer Radical Polymerization". Journal of Polymer Science: Part A: Polymer Chemistry. vol. 38. 2000. pp. 2023-2031.

Shipp, Devon A.; Wang, Jen-Lung. Matyjaszewski, Krzysztof. "Synthesis of Acrylate and Methacrylate Block Copolymers Using Atom Transfer Radical Polymerization". Macromolecules. vol. 31. 1998. pp. 8005-8008.

David, Ghislain; Robin, Jean-Jacques; Desmazes-Lacroix, Patrick. "Synthesis of Thermoplastic Elastomer Based on Polystyrene Polydimethysiloxane Block Copolymers". Polymer Preprints. vol. 43. No. 2. 2002. pp. 1095-1096.

Matyjaszewski, Krzysztof; Ziegler, Michael J.; Arehart, Stephen V.; Greszta; Pakula, Tadeusz. "Gradient Copolymers by Atom Transfer Radical Copolymerization". J. Phys. Org. Chem. vol. 13. 2000. pp. 775-786.

Miller, Peter J.; Matyjaszewski, Krzysztof. "Atom Transfer Radical Polymerization of (Meth) Acrylates From Poly(Dimethylsiloxane) Macroinitiators". Macromolecules. vol. 32. 1999. 8760-8767.

Pyun, Jeffrey; Matyjaszewski. "Synthesis of Nanocomposite Organic/Inorganic Hybrid Materials Using Controlled/"Living" Radical Polymerization". Chem. Mater. vol. 13. 2001. pp. 3436-3448.

"Morphology of Block Copolymers". Block Copolymers and Thermoplastic Elastomers. pp. 282-287.

Hemmerich, Karl J. "Polymer Materials Selection for Radiation-Sterilized Products". Medical Device & Diagnostic Industry Magazine. Feb. 2000. pp. 78-89.

* cited by examiner

MEDICAL DEVICES CONTAINING RADIATION RESISTANT BLOCK COPOLYMER

FIELD OF THE INVENTION

The present invention relates generally to radiation-resistant medical devices which contain polymer regions for release of therapeutic agents. The present invention also relates to radiation-resistant block copolymer materials for use in connection with insertable or implantable medical devices.

BACKGROUND OF THE INVENTION

Numerous polymer-based medical devices have been developed for the delivery of therapeutic agents to the body. In accordance with some typical delivery strategies, a therapeutic agent is provided within a polymeric carrier layer and/or beneath a polymeric barrier layer that is associated with a medical device. Once the medical device is placed at the desired location within a patient, the therapeutic agent is released from the medical device at a rate that is dependent upon the nature of the polymeric carrier and/or barrier layer.

Materials which are suitable for use in making implantable or insertable medical devices typically exhibit one or more of the qualities of exceptional biocompatibility, extrudability, elasticity, moldability, good fiber forming properties, tensile strength, durability, and the like. Moreover, the physical and chemical characteristics of the device materials can play an important role in determining the final release rate of the therapeutic agent.

As a specific example, block copolymers of polyisobutylene and polystyrene, for example, polystyrene-polyisobutylene-polystyrene triblock copolymers (SIBS copolymers), which are described in U.S. Pat. No. 6,545,097 to Pinchuk et al., which is hereby incorporated by reference in its entirety, have proven valuable as release polymers in implantable or insertable drug-releasing medical devices. As described in Pinchuk et al., the release profile characteristics of therapeutic agents such as paclitaxel from SIBS copolymer systems demonstrate that these copolymers are effective drug delivery systems for providing therapeutic agents to sites in vivo.

These copolymers are particularly useful for medical device applications because of their excellent strength, biostability and biocompatibility, particularly within the vasculature. For example, SIBS copolymers exhibit high tensile strength, which frequently ranges from 2,000 to 4,000 psi or more, and resist cracking and other forms of degradation under typical in vivo conditions. Biocompatibility, including vascular compatibility, of these materials has been demonstrated by their tendency to provoke minimal adverse tissue reactions (e.g., as measured by reduced macrophage activity). In addition, these polymers are generally hemocompatible as demonstrated by their ability to minimize thrombotic occlusion of small vessels when applied as a coating on coronary stents.

In addition, these polymers possess many interesting physical and chemical properties sought after in medical devices, due to the combination of the polyisobutylene and polystyrene blocks. Polyisobutylene has a low glass transition temperature ($T_g$) and is soft and elastomeric at room (and body) temperature. Polystyrene, on the other hand, has a much higher $T_g$ and is thus hard at these temperatures. Polystyrene is also thermoplastic in nature, opening up a wide range of processing capabilities. Depending upon the relative amounts of polystyrene and polyisobutylene, the resulting copolymer can be formulated to have a range of hardness, for example, from as soft as about Shore 10A to as hard as about Shore 100D.

Whether the system comprises a SIBS copolymer or other biocompatible polymers, these materials, once incorporated into a finished medical device, typically undergo a sterilization process. Two prevalent sterilization processes are exposure to ethylene oxide (EtO) and irradiation by, for example, gamma or electron beam radiation. For several decades, sterilization using ethylene oxide has been the method of choice for sterilizing medical devices such as catheters, mechanical heart valves, sutures, adhesive bandages, tracheostomy tubes, and so on. The primary advantages associated with the use of EtO sterilization are the low processing temperature and the wide range of compatible materials. However, the toxicity of the gas, its potential carcinogenicity, and concerns over residuals in the product and the manufacturing environment have subjected EtO use to ever increasing regulatory scrutiny and control and continues to escalate the cost of EtO sterilization. In addition, EtO is highly reactive and may interact with or otherwise adversely affect various therapeutic agents present in a medical device.

Radiation sterilization, whether by gamma rays, X-rays, accelerated electrons, or other means, is a widely-used alternative method for sterilizing medical devices. Products to be sterilized are typically exposed to gamma rays from a Co-60 or a Cs-137 source or to machine accelerated electrons until the desired dose is received. No toxic agents are involved, and products may be released for sale on the basis of documentation that the desired dose is delivered. For the sterilization of polymeric medical devices, a typical radiation dose of about 1.0-5.0 Mrad (10-50 kGy) or higher, is employed.

Radiation sterilization, however, may modify many important physical and chemical properties of polymeric materials such as the molecular weight, chain length, entanglement, polydispersity, branching, pendant functionality, and chain termination. These changes in the properties may impact, for instance, the drug-eluting properties of the polymers and impair the performance of a polymer for a specific use. For example, from a product use standpoint, mechanical properties are important characteristics that may be adversely affected by irradiation of polymers. These properties include tensile strength, elastic modulus, impact strength, shear strength, and elongation.

For example, when polymers are exposed to radiation, two basic reactions may occur: (1) chain scission (i.e., a random rupturing of bonds) of polymer molecules and (2) crosslinking of polymer molecules. Crosslinking generally results in the formation of larger, three-dimensional polymer structures. Chain scission, on the other hand, generally results in a decrease in the molecular weight of the polymer molecules. Although both of these reactions commonly occur as polymeric materials are subjected to ionizing radiation, one reaction frequently predominates within a specific polymer. As a result of chain scission, very-low-molecular-weight fragments, gas evolution, and unsaturated bonds may appear. Cross-linking generally results in an initial increase in tensile strength, while impact strength decreases and the polymer becomes more brittle with increased dose.

For polymers with carbon-carbon backbones, it has been observed that cross-linking generally will occur if the carbons have one or more hydrogen atoms attached, whereas chainscission generally occurs at tetra-substituted carbons. Polymers containing aromatic molecules are generally more resistant to radiation degradation than are aliphatic polymers; this is true whether or not the aromatic group is directly in the chain backbone or not. Thus, both polystyrenes, with a pendant aromatic group, and polyimides, with an aromatic group directly in the polymer backbone, are relatively resistant to high doses (>4000 kGy). On the other hand, homopolymers and copolymers containing polyisobutylene such as a SIBS copolymer are generally more susceptible to radiation effects and may undergo chain scission during irradiation, especially at the radiation levels typically used for medical device sterilization (e.g., about 2.5 Mrad). A summary of the effects of radiation on polymer properties, such as loss of elongation, for a number of common thermoplastics and thermosets is provided in "Polymer Materials Selection for Radiation-Sterilized Products" by Karl J. Hemmerich, *Medical Device & Diagnostic Industry Magazine*, February 2000, pp. 78-89, the entire contents of which are hereby incorporated by reference.

Radiation issues are particularly pronounced in medical devices having thin polymer coatings. This is especially true where a radiation sensitive polymer such as a SIBS copolymer is provided in the form of a thin coating on the surface of an expandable medical device such as a stent or balloon. For example, radiation can lead to an unacceptable increase in the surface tack of the SIBS copolymer, which can in turn cause defects in the polymer when it is expanded (e.g., in situations where it is in the form of a coating on the surface of an expandable stent or balloon).

Additionally, SIBS copolymers present special synthesis challenges. Currently, SIBS copolymers are synthesized by a living cationic polymerization process, a complex process that requires stringent reaction conditions and low temperatures. Ionic (cationic and anionic) polymerizations typically require reaction conditions free of moisture, oxygen, as well as impurities. To date, only a limited number of monomers have been polymerized by a living cationic polymerization process, thus restricting the ability to vary the chemical composition of polymers and copolymers produced by this process. Further, the experimental rigor generally involved in ionic polymerizations is often too costly for industrial use and free radical routes are preferred.

Hence, it would be advantageous to provide polymers that have various properties that are analogous to those of SIBS copolymers (e.g., drug release characteristics and biostability/biocompatibility) but which also exhibit improved immunity to radiation-based changes in polymer properties and are easier to synthesize using a wider array of monomer materials.

SUMMARY OF THE INVENTION

These and other challenges of the prior art are addressed by the present invention which provides a radiation-sterilized medical device comprising (a) a release region and (b) a therapeutic agent. The release region comprises a radiation resistant copolymer that further comprises (i) a low $T_g$ hydrocarbon polymer block and (ii) a high $T_g$ polymer block.

The present invention is advantageous in that a medical device can be provided, which is resistant to the damaging effects of radiation sterilization.

Another advantage of the present invention is that implantable or insertable medical devices can be provided, which result in controlled release of a therapeutic agent.

Yet another advantage of the present invention is that biostable, radiation-resistant polymeric materials are provided which avoid the limitations of standard synthesis methods for preparing polyisobutylene via a living cationic polymerization process.

These and other embodiments and advantages of the present invention will become immediately apparent to those of ordinary skill in the art upon review of the Detailed Description and claims to follow.

DETAILED DESCRIPTION OF THE INVENTION

Figure 1:
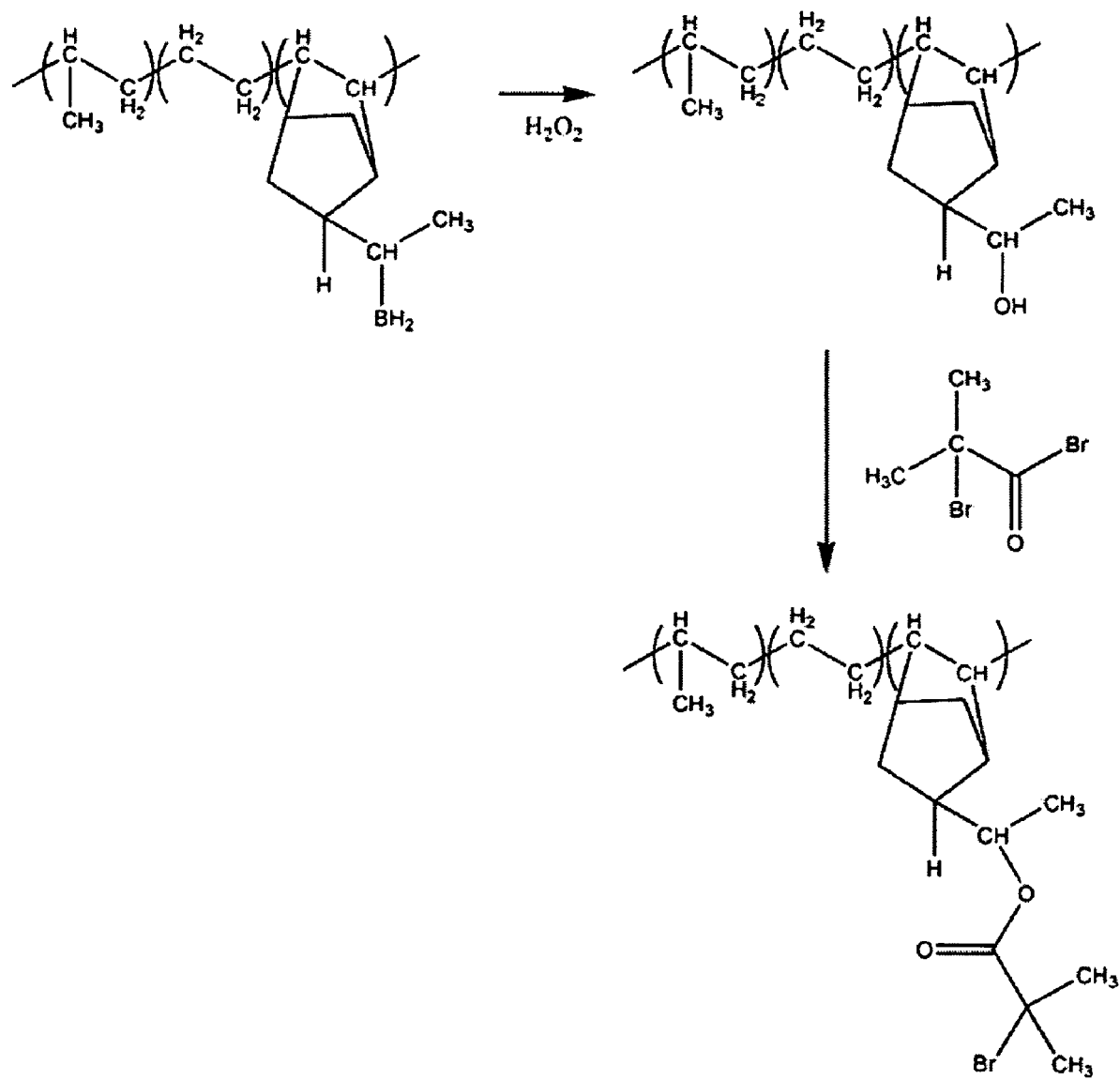
FIG. 1 schematically illustrates the synthesis of an EPDM macroinitiator by the reaction of an EPDM molecule having a hydroxyl end functional group with 2-bromo-isobutyryl bromide to form an EPDM with a bromoester end functional group (EPDM macroinitiator).

The present invention relates to radiation-resistant copolymers that are useful for the delivery of a therapeutic agent in connection with an intravascular or intervascular medical device.

According to an aspect of the present invention, a radiation-sterilized medical device is provided, which includes: (a) a release region and (b) one or more therapeutic agents. The release region further includes at least one radiation-resistant copolymer that contains (i) one or more low $T_g$ hydrocarbon polymer blocks and (ii) one or more high $T_g$ polymer blocks.

Release regions for use in accordance with the present invention include carrier regions and barrier regions. By "carrier region" is meant a release region which further comprises a therapeutic agent and from which the therapeutic agent is released. For example, in some embodiments, a carrier region is disposed over all or a portion of a medical device substrate. In other embodiments, a carrier region constitutes the entirety of the medical device.

By "barrier region" is meant a region which is disposed between a source of therapeutic agent and a site of intended release, and which controls the rate at which therapeutic agent is released. For example, in some embodiments, the medical device is provided with a barrier region that surrounds a source of therapeutic agent. In other embodiments, a barrier region is disposed over a source of therapeutic agent, which is in turn disposed over all or a portion of a medical device substrate.

Hence, in various embodiments, release regions for use in accordance with the present invention are in the form of a release layers, which cover all or a part of a medical device substrate. As used herein a "layer" of a given material is a region of that material whose thickness is small compared to both its length and width. As used herein a layer need not be planar or conformal (for example, taking on the contours of an underlying substrate). Layers can be discontinuous (e.g., patterned). Terms such as "film," "layer" and "coating" may be used interchangeably herein.

Medical devices for use in conjunction with the present invention include essentially any medical device for which controlled release of a therapeutic agent is desired. Examples of medical devices include implantable or insertable medical devices, for example, catheters (e.g., renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filter coils (including Guglilmi detachable coils and metal coils), vascular grafts, myocardial plugs, patches, pacemakers and pacemaker leads, heart valves, biopsy devices, and any coated substrate (which can comprise, for example, glass, metal, polymer, ceramic and combinations thereof) that is implanted or inserted into the body and from which therapeutic agent is released. Examples of medical devices further include patches for delivery of therapeutic agent to intact skin and broken skin (including wounds); sutures, suture anchors, anastomosis clips and rings, tissue staples and ligating clips at surgical sites; orthopedic fixation devices such as interference screws in the ankle, knee, and hand areas, tacks for ligament attachment and meniscal repair, rods and pins for fracture fixation, screws and plates for craniomaxillofacial repair; dental devices such as void fillers following tooth extraction and guided-tissue-regeneration membrane films following periodontal surgery; and tissue engineering scaffolds for cartilage, bone, skin and other in vivo tissue regeneration.

The medical devices of the present invention include medical devices that are used for either systemic treatment or for the localized treatment of any mammalian tissue or organ. Non-limiting examples are tumors; organs including the heart, coronary and peripheral vascular system (referred to overall as "the vasculature"), lungs, trachea, esophagus, brain, liver, kidney, bladder, urethra and ureters, eye, intestines, stomach, pancreas, vagina, uterus, ovary, and prostate; skeletal muscle; smooth muscle; breast; dermal tissue; cartilage; and bone.

Specific examples of medical devices for use in conjunction with the present invention include vascular stents, which deliver therapeutic agent into the vasculature for the treatment of restenosis. In these embodiments, the release region is typically provided over all or a portion of a stent substrate, and is typically in the form of a carrier layer (in which case therapeutic agent is disposed within the release layer) or a barrier layer (in which case the release layer is disposed over a therapeutic-agent containing region).

As used herein, "treatment" refers to the prevention of a disease or condition, the reduction or elimination of symptoms associated with a disease or condition, or the substantial or complete elimination of a disease or condition. Preferred subjects are mammalian subjects and more preferably human subjects.

By "radiation sterilized" is meant that the medical device has been exposed to a quantity of radiation that is effective to kill pathogens associated with the medical device. The radiation that is used to sterilize the medical devices of the present invention is typically ionizing radiation, such as gamma radiation, X-ray radiation, or electron beam radiation. For example, sterilizing radiation doses for medical devices typically ranges between 100,000 rads and 100 Mrad. This includes, for example, 100,000 rads, 500,000 rads, 1,000,000 rads (1 Mrad), 2.5 Mrad, 5 Mrad, 7.5 Mrad, 10 Mrad, 20 Mrad, 50 Mrad and 100 Mrad, as well as ranges between any two of these doses, for example, 100,000 rad to 1 Mrad, 500,000 rad to 20 Mrad, and so forth, with 1 Mrad to 10 Mrad being a particularly beneficial range.

By "radiation stable copolymer" is meant that, at typical radiation sterilization doses employed as discussed above (e.g., 1 Mrad to 10 Mrad), the copolymer does not undergo changes in either molecular weight (e.g., Mw, Mn, via either crosslinking or chain scission) or morphology that significantly change a functional property of a device or coating (e.g., drug delivery properties or mechanical properties such as elongation modulus) that negatively impacts its performance for its intended application.

As used herein, polymers are molecules containing one or more chains, which contain multiple copies of one or more constitutional units. An example of a common polymer is polystyrene

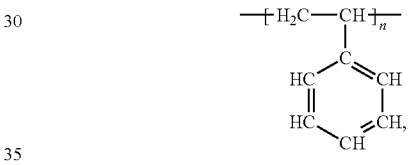

where n is an integer, typically an integer of 10 or more, more typically on the order of 10's, 100's, 1000's or even more, in which the constitutional units in the chain correspond to styrene monomers:

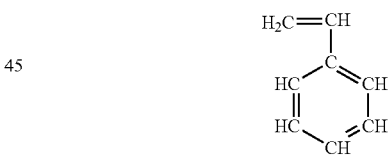

(i.e., they originate from, or have the appearance of originating from, the polymerization of styrene monomers in this case, the addition polymerization of styrene monomers). As used herein, copolymers are polymers that contain at least two dissimilar constitutional units.

As used herein, a polymer "block" is a grouping of 10 or more constitutional units, commonly 20 or more, 50 or more, 100 or more, 200 or more, 500 or more, or even 1000 or more units. A "chain" is a linear (unbranched) grouping of 10 or more constitutional units (i.e., a linear block).

As noted above, the medical devices of the present invention are radiation-sterilized and include one or more radiation resistant copolymers containing (a) one or more low $T_g$ hydrocarbon polymer blocks and (b) one or more high $T_g$ polymer blocks.

A "low $T_g$ polymer block" is a polymer block that displays one or more glass transition temperatures ($T_g$), as measured by any of a number of techniques including differential scanning calorimetry (DSC), dynamic mechanical analysis (DMA), or dielectric analysis (DEA), that is below ambient temperature, more typically below 25° C., below 0° C., below −25° C., or even below −50° C. "Ambient temperature" is typically 25° C.-45° C., more typically body temperature (e.g., 35° C.-40° C.). As a result of their low glass transition temperature, low $T_g$ polymer blocks are typically elastomeric at ambient temperature. Homopolymers of some low $T_g$ polymer blocks, such as linear or branched silicone (e.g. polydimethylsiloxane), are viscous liquids or millable gums at room temperature and become elastomeric upon covalent cross-linking.

Conversely, an elevated or "high $T_g$ polymer block" is a polymer block that displays one or more glass transition temperatures, as measured by any of a number of techniques including differential scanning calorimetry, dynamic mechanical analysis, or thermomechanical analysis, which is above ambient temperature, more typically more typically above 50° C., above 60° C., above 70° C., above 80° C., above 90° C. or even above 100° C.

Hence, due to the presence of one or more low $T_g$ blocks and one or more high $T_g$ polymer blocks, the copolymers of the present invention will typically have one or more glass transition temperatures below ambient temperature and one or more glass transition temperatures above ambient temperature. This typically results in the formation of rubbery and hard phases within the release region at ambient temperatures.

A "hydrocarbon polymer block" is a block containing repeating hydrocarbon units (i.e., repeating units containing carbon and hydrogen atoms only). The hydrocarbon polymer block may be present in the copolymer, for example, as a midblock or as an endblock. It may be provided in a variety of configurations, including cyclic, linear and branched configurations. Branched configurations include star-shaped configurations (e.g., configurations in which three or more chains emanate from a single branch point), comb configurations (e.g., configurations having a main chain and a plurality of side chains) and dendritic configurations (e.g., arborescent and hyperbranched polymers). The chain or chains forming the hydrocarbon polymer block(s) may contain, for example, (a) a repeating series of hydrocarbon units of a single type, or (b) a series of hydrocarbon units of two or more types, for instance, arranged in a repeating (e.g., alternating), random, statistical or gradient distribution.

A "telechelic" polymer as used herein is a polymer that contains at least two functional groups per molecule, one at each terminus of the polymer. The functional groups on the termini of the polymer can be the same (such as two hydroxyl groups) or different (such as one hydroxyl group and one amino group). The preparation of telechelic polymers is taught in the prior art. For example, the preparation of telechelic star polymers is described in U.S. Pat. No. 5,919,870, assigned to FMC Corporation, the entire contents of which are hereby incorporated by reference.

As will be appreciated by one of skill in the art, the block copolymers described herein, including those described in the preceding paragraphs, may be recovered from the reaction mixtures by any of the usual techniques, including but not limited to, evaporation of solvent, precipitation with a non-solvent such as an alcohol or alcohol/acetone mixture, followed by drying, and so forth. In addition, purification of the copolymer can be performed by sequential extraction in aqueous media, both with and without the presence of various alcohols, ethers and ketones.

Specific examples of hydrocarbon polymer blocks from which the low $T_g$ hydrocarbon polymer blocks can be selected include blocks which contain polymers of alkenes, including polymers of olefins (i.e., hydrocarbon monomers containing a single >C=C< double bond), polymers of dienes (i.e., hydrocarbon monomers containing two >C=C< double bonds), also called diolefins, or polymers of both olefins and dienes, are provided below.

For example, the low $T_g$ hydrocarbon polymer block can comprise an EPDM (ethylene-propylene-diene monomer) copolymer block, which contain units formed from two olefins (ethylene and propylene) and one or more dienes (e.g., vinyl norbornene or ethylidene norbornene), which are illustrated in turn in the following structure:

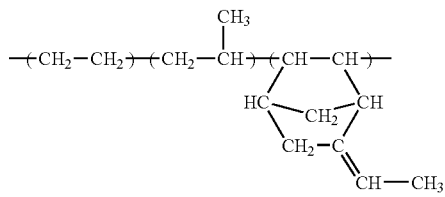

Commercially prepared EPDM copolymer blocks include Vistalon™ polymers available from Exxon-Mobil. The synthesis of EPDM copolymers is well-known in the art, including preparation via Ziegler-Natta polymerization using homogeneous catalyst compositions based on vanadium, titanium, zirconium, and metallocenes. Details of the preparation of EPDM copolymers are given in U.S. Pat. No. 6,486,278, assigned to ExxonMobil Chemical Patents Inc., the entire contents of which are hereby incorporated by reference. Synthesis typically involves contacting ethylene, one or more olefin monomers, and one or more cyclic diolefin monomers, with a catalyst composition prepared from a catalyst activator and a catalyst, by a solution polymerization process.

In addition to propylene and ethylene, a wide range of olefins are suitable for use in the preparation of the EPDM, including for example, $C_3$ to $C_{20}$ α-olefins such as 1-butene, 1-pentene, 1-hexene, 1-octene, and 1-decene, constrained-ring cyclic monoolefins such as cyclobutene, cyclopentene, norbornene, alkyl substituted norbornene, and alkenyl-substituted norbornene.

The diene monomers, or diolefin components of the EPDM copolymer can be a mixture of one or more cyclic diolefins having from about 6 to about 15 carbon atoms, including 1) single ring alicyclic dienes such as 1,3-cyclopentadiene, 2) multi-ring alicyclic fused and bridged ring dienes such as tetrahydroindene, dicyclopentadiene, cycloalkenyl and cycloalkylidene norbornenes such as 5-methylene-2-norbornene, 5-ethylidene-2-norbornene, 5-isopropylidene-2-norbornene, 5-(4-cyclopentenyl)-2-norbornene, 5-cyclohexylidene-2-norbornene, 5-vinyl-2-cyclododecene, and 3) cycloalkenyl-substituted alkenes, such as allyl cyclohexene, vinyl cyclooctene, allyl cyclohexene, vinyl cyclooctene, allyl cyclodecene, and vinyl cyclododecene.

As a further example, the low $T_g$ hydrocarbon polymer block can comprise the following polydiene and polyolefin blocks, as well as variants such as hydrogenated forms of same:

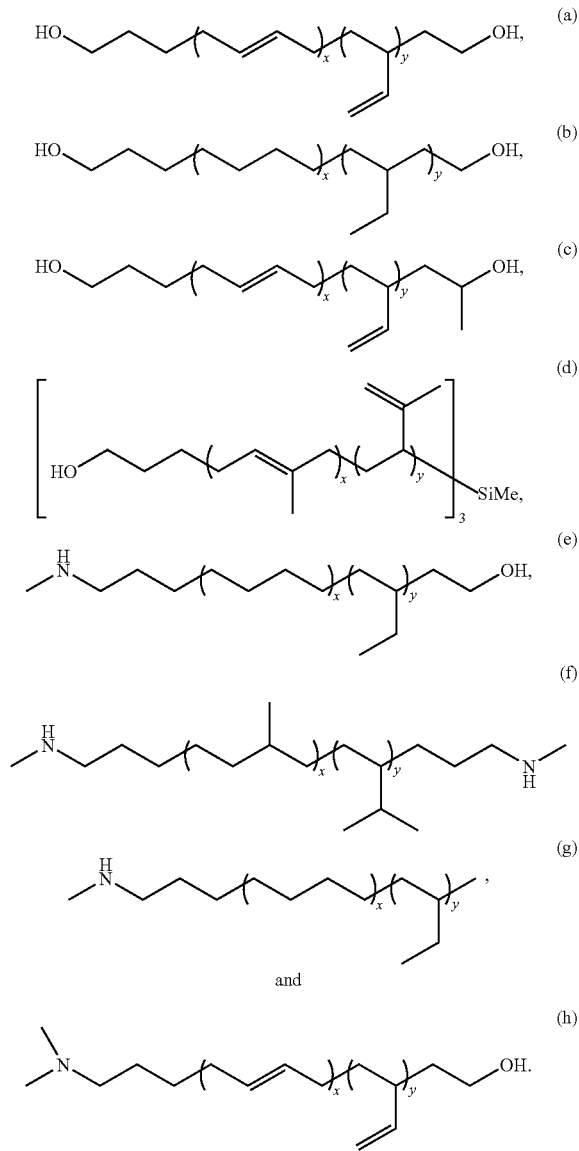

The low $T_g$ hydrocarbon polymer block may also be formed from conjugated diene monomers, including but not limited to, 1,3-butadiene, 2,3-dimethyl-1,3butadiene, 2-methyl-1,3-butadiene (isoprene), 3-ethenyl-1,6-heptadiene, 5-ethyl-1,3,5-heptatriene, 5-methyl-1,3-cycloheptadiene, 2,3-dimethyl-1,3-butadiene, 1,4-diphenyl-1,3-butadiene, cyclopentadiene, cyclohexadiene, cycloheptadiene, cyclooctadiene, anthracene, chloroprene and the like. The invention also includes hydrogenated forms of polymer blocks formed from these monomers.

Like the low $T_g$ hydrocarbon polymer blocks described above, the high $T_g$ polymer blocks may be present in the copolymers, for example, as midblocks or as endblocks. The high $T_g$ polymer blocks may be provided in a variety of configurations, including cyclic, linear and branched configurations. Branched configurations include star-shaped configurations (e.g., configurations in which three or more chains emanate from a single branch point), comb configurations (e.g., configurations having a main chain and a plurality of branching side chains) and dendritic configurations (e.g., arborescent and hyperbranched polymers). The high $T_g$ polymer blocks may contain, for example, a repeating series of units of a single type, a series of units of two or more types in a repeating (e.g., alternating), random, statistical or gradient distribution, and so forth.

Specific examples of high $T_g$ polymer blocks from which high $T_g$ polymer blocks can be selected include homopolymer and copolymer blocks formed from (or having the appearance of being formed from) the following: various vinyl aromatic monomers, other vinyl monomers, other aromatic monomers, methacrylic monomers, and acrylic monomers. Numerous specific examples are listed below. The $T_g$ values are published values for homopolymers of the listed monomeric unit.

Vinyl aromatic monomers are monomers having aromatic and vinyl moieties, including unsubstituted monomers, vinyl-substituted monomers and ring-substituted monomers. Several specific vinyl aromatic monomers follow: (a) unsubstituted vinyl aromatics, such as atactic styrene ($T_g$ 100° C.), isotactic styrene ($T_g$ 100° C.) and 2-vinyl naphthalene ($T_g$ 151° C.), (b) vinyl substituted aromatics such as methyl styrene, (c) ring-substituted vinyl aromatics including (i) ring-alkylated vinyl aromatics such as 3-methylstyrene ($T_g$ 97° C.), 4-methylstyrene ($T_g$ 97° C.), 2,4-dimethylstyrene ($T_g$ 112° C.), 2,5-dimethylstyrene ($T_g$ 143° C.), 3,5-dimethylstyrene ($T_g$ 104° C.), 2,4,6-trimethylstyrene ($T_g$ 162° C.), and 4-tert-butylstyrene ($T_g$ 127° C.), (ii) ring-alkoxylated vinyl aromatics, such as 4-methoxystyrene ($T_g$ 113° C.) and 4-ethoxystyrene ($T_g$ 86° C.), (iii) ring-halogenated vinyl aromatics such as 2-chlorostyrene ($T_g$ 119° C.), 3-chlorostyrene ($T_g$ 90° C.), 4-chlorostyrene ($T_g$ 110° C.), 2,6-dichlorostyrene ($T_g$ 167° C.), 4-bromostyrene ($T_g$ 118° C.) and 4-fluorostyrene ($T_g$ 95° C.) and (iv) ester-substituted vinyl aromatics such as 4-acetoxystyrene ($T_g$ 116° C.).

Other specific vinyl monomers include: (a) vinyl alcohol ($T_g$ 85° C.); (b) vinyl esters such as vinyl benzoate ($T_g$ 71° C.), vinyl 4-tert-butyl benzoate ($T_g$ 101° C.), vinyl cyclohexanoate ($T_g$ 76° C.), vinyl pivalate ($T_g$ 86° C.), vinyl trifluoroacetate ($T_g$ 46° C.), vinyl butyral ($T_g$ 49° C.), (c) vinyl amines such as 2-vinyl pyridine ($T_g$ 104° C.), 4-vinyl pyridine ($T_g$ 142° C.), and vinyl carbazole ($T_g$ 227° C.), (d) vinyl halides such as vinyl chloride ($T_g$ 81° C.) and vinyl fluoride ($T_g$ 40° C.); (e) alkyl vinyl ethers such as tert-butyl vinyl ether ($T_g$ 88° C.) and cyclohexyl vinyl ether ($T_g$ 81° C.), and (f) other vinyl compounds such as 1-vinyl-2-pyrrolidone ($T_g$ 54° C.) and vinyl ferrocene ($T_g$ 189° C.).

Specific aromatic monomers, other than vinyl aromatics, include: acenaphthalene ($T_g$ 214° C.) and indene ($T_g$ 85° C.).

Specific methacrylic monomers include (a) methacrylic acid ($T_g$ 228° C.), (b) methacrylic acid salts such as sodium methacrylate ($T_g$ 310° C.), (c) methacrylic acid anhydride ($T_g$ 159° C.), (d) methacrylic acid esters (methacrylates) including (i) alkyl methacrylates such as atactic methyl methacrylate ($T_g$ 105-120° C.), syndiotactic methyl methacrylate ($T_g$ 115° C.), ethyl methacrylate ($T_g$ 65° C.), isopropyl methacrylate ($T_g$ 81° C.), isobutyl methacrylate ($T_g$ 53° C.), t-butyl methacrylate ($T_g$ 118° C.) and cyclohexyl methacrylate ($T_g$ 92° C.), (ii) aromatic methacrylates such as phenyl methacrylate ($T_g$ 110° C.) and including aromatic alkyl methacrylates such as benzyl methacrylate ($T_g$ 54° C.), (iii) hydroxyalkyl methacrylates such as 2-hydroxyethyl methacrylate ($T_g$ 57° C.) and 2-hydroxypropyl methacrylate ($T_g$ 76° C.), (iv) additional methacrylates including isobornyl methacrylate ($T_g$ 110° C.) and trimethylsilyl methacrylate ($T_g$ 68° C.), and (e) other methacrylic-acid derivatives including methacrylonitrile ($T_g$ 120° C.).

Specific acrylic monomers include (a) acrylic acid ($T_g$ 105° C.), its anhydride and salt forms, such as potassium acrylate ($T_g$ 194° C.) and sodium acrylate ($T_g$ 230° C.); (b) certain acrylic acid esters such as tert-butyl acrylate ($T_g$ 43-107° C.) ($T_m$ 193° C.), hexyl acrylate ($T_g$ 57° C.) and isobornyl acrylate ($T_g$ 94° C.); (c) acrylic acid amides such as acrylamide ($T_g$ 165° C.), N-isopropylacrylamide ($T_g$ 85-130° C.) and N,N dimethylacrylamide ($T_g$ 89° C.); and (d) other acrylic-acid derivatives including acrylonitrile ($T_g$ 125° C.).

In some particularly beneficial embodiments, the block copolymers for use in the present invention have one of the following general structures: BAB or ABA (triblock), B(AB)n or A(BA)n (alternating block), or X-(AB)n or X-(BA)n (including diblock, triblock, and other radial block copolymers), where A is a low $T_g$ block and B is a high $T_g$ block, n is a positive whole number and X is a starting seed molecule. Where the block copolymer is of the formula X-AB)n or X-(BA)n and where n=1, the resulting structure is frequently called a diblock, where n=2, the structure is called a triblock (it is common to disregard the presence of small entities such as the seed molecule X in describing such polymers), and where n=3 or greater, these structures are commonly referred to as star-shaped block copolymers.

One preferred group of block copolymers has (a) a hydrocarbon polymer midblock or main chain, including the examples listed above, and (b) one or more high $T_g$ endblocks or side chains, which can be for example blocks of polystyrene or poly(alkyl methacrylate).

The release regions of the present invention optionally include a supplemental polymer in addition to the above-described copolymers. A variety of polymers are available for use as supplemental polymers in the release regions of the present invention. For example, the supplemental polymer may be a homopolymer or a copolymer (including alternating, random, statistical, gradient and block copolymers), may be cyclic, linear or branched (e.g., polymers have star, comb or dendritic architecture), may be natural or synthetic, and may be thermoplastic or thermosetting. Supplemental polymers for the practice of the invention may be selected, for example, from the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the above.

Numerous techniques are available for forming the polymeric release regions of the present invention. For example, where the selected copolymer (and supplemental polymer, if any) has thermoplastic characteristics, a variety of standard thermoplastic processing techniques can be used to form the polymeric release region, including compression molding, injection molding, blow molding, spinning, vacuum forming and calendaring, as well as extrusion into sheets, fibers, rods, tubes and other cross-sectional profiles of various lengths.

Using these and other techniques, entire devices or portions thereof can be made. For example, an entire stent can be extruded using the above techniques. As another example, a coating can be provided by extruding a coating layer onto a pre-existing stent. As yet another example, a coating can be co-extruded along with an underlying stent body.

If the therapeutic agent is stable at processing temperatures, then it can be combined with the copolymer prior to thermoplastic processing, producing a therapeutic-agent containing carrier region. If not, then a carrier region can nonetheless be formed by subsequent introduction of therapeutic agent, for example, as discussed below.

Polymeric release regions can also be formed using solvent-based techniques in which copolymer (and supplemental polymer, if any) is first dissolved or dispersed in a solvent and the resulting mixture is subsequently used to form the polymeric release region.

Where solvent-based techniques are used, the solvent system that is selected will contain one or more solvent species. The solvent system preferably is a good solvent for the copolymer and, where included, for the supplemental polymer and therapeutic agent as well. The particular solvent species that make up the solvent system may also be selected based on other characteristics including drying rate and surface tension.

Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

In many embodiments, a mixture containing solvent, copolymer and supplemental polymer, if any, is applied to a substrate to form a release region. For example, the substrate can be all or a portion of an implantable or insertable medical device, such as a stent, to which a release layer is applied. On the other hand, the substrate can also be, for example, a template from which the polymeric release region is removed after solvent elimination. Such template-based techniques are particularly appropriate for forming simple objects such as sheets, tubes, cylinders and so forth, which can be easily removed from a template substrate.

In other techniques, for example, fiber forming techniques, the polymeric release region is formed without the aid of a substrate or template.

Where appropriate, techniques such as those listed above can be repeated or combined to build up a release layer to a desired thickness. The thickness of the release layer can be varied in other ways as well. For example, in one preferred process, solvent spraying, coating thickness can be increased by modification of coating process parameters, including increasing spray flow rate, slowing the movement between the substrate to be coated and the spray nozzle, providing repeated passes and so forth.

Where a carrier region is formed (as opposed to, for example, a barrier region), a therapeutic agent can be dissolved or dispersed in the polymer/solvent mixture if desired, and hence co-established with the carrier region. In other embodiments, on the other hand, the therapeutic agent can be dissolved or dispersed within a solvent, and the resulting solution contacted with a polymer region that is previously formed using, for example, one or more of the application techniques described above (e.g., dipping, spraying, etc.).

Barrier layers, on the other hand, are formed over a therapeutic-agent-containing region, for example, using solvent-based techniques such as those discussed above in which the copolymer and supplemental polymer, if any, are first dissolved or dispersed in a solvent, and the resulting mixture is subsequently used to form the barrier layer. The barrier layer serves, for example, as a boundary layer to retard diffusion of the therapeutic agent, for example, acting to prevent a burst phenomenon whereby much of the therapeutic agent is released immediately upon exposure of the device or a portion of the device to the implant or insertion site.

In some embodiments, the therapeutic-agent-containing region beneath the barrier region will comprise one or more polymers such as those described elsewhere herein. (In these embodiments, the polymeric composition of the barrier region may, or may not be the same as the polymeric composition of the underlying therapeutic-agent-containing region.) As such, the therapeutic-agent-containing region can also be established using solvent-based techniques (e.g., dipping, spraying, etc.) such as those discussed above. In other embodiments, the therapeutic-agent-containing region beneath the barrier layer is established without an associated polymer. In this case, the therapeutic agent can simply be dissolved or dispersed in a solvent or liquid, and the resulting solution/dispersion can be contacted with a substrate again using, for instance, one or more of the above-described application techniques.

Where the release region is formed using a solvent-based technique, it is preferably dried after application to remove the solvents. The release region typically further conforms to any underlying surface during the drying process.

"Therapeutic agents," "pharmaceutically active agents," "pharmaceutically active materials," "drugs," and other related terms may be used interchangeably herein and include genetic therapeutic agents, non-genetic therapeutic agents and cells. Therapeutic agents may be used singly or in combination. Therapeutic agents may be used singly or in combination. Therapeutic agents may be, for example, nonionic or they may be anionic and/or cationic in nature.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; and (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin.

Preferred non-genetic therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomycin D, Resten-NG, Ap-17, abciximab, clopidogrel and Ridogrel, among others.

Exemplary genetic therapeutic agents for use in connection with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers such as polyvinylpyrrolidone (PVP), SPI017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

Therapeutic agents also include ablation agents, sufficient amounts of which will result in necrosis (death) of undesirable tissue, such as malignant tissue, prostatic tissue, and so forth. Examples include osmotic-stress-generating agents, for example, salts such as sodium chloride or potassium chloride; organic solvents, particularly those such as ethanol, which are toxic in high concentrations, while being well tolerated at lower concentrations; free-radical generating agents, for example, hydrogen peroxide, potassium peroxide or other agents that can form free radicals in tissue; basic agents such as sodium hydroxide; acidic agents such as acetic acid and formic acid; enzymes such as collagenase, hyaluronidase, pronase, and papain; oxidizing agents, such as sodium hypochlorite, hydrogen peroxide or potassium peroxide; tissue fixing agents, such as formaldehyde, acetaldehyde or glutaraldehyde; and naturally occurring coagulants, such as gengpin.

A wide range of therapeutic agent loadings can be used in connection with the dosage forms of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

As will be appreciated by one of skill in the art, the release profile associated with the release region can be modified, for example, by altering the chemical composition of the release region (e.g., by changing the chemical composition of the copolymer, by blending one or more supplementary polymers with the copolymer, etc.) and/or by changing the physical structure of the release region or surrounding regions (e.g., by adding a separate barrier layer that contains one or more polymers, etc.).

For instance, according to various aspects of the present invention, the release profile associated with a release region of the medical device can be modified in a number of ways, including, but not limited to, (a) changing the composition of the low $T_g$ polymer block(s) and/or high $T_g$ polymer blocks within the copolymer, thus changing, for example, the biostability, hydrophilicity and/or hydrophobicity of the copolymer, (b) changing the molecular weight of the low $T_g$ or high $T_g$ polymer blocks and/or other polymer blocks, (c) changing the ratio of the low $T_g$ polymer block(s) relative to the high $T_g$ polymer block(s), (d) changing the distribution of the low $T_g$ and high $T_g$ polymer blocks (e.g., midblock vs. endblock) within the polymer and/or (e) changing the architecture of the copolymer (e.g., a linear copolymer vs. a branched copolymer), among others.

The release profile associated with a release region of the medical device can also be modified by changing the number, order, thickness, or position of carrier and barrier regions with respect to one another. For example, the release profile can be modified by varying the thickness of the release region. Moreover, multiple release regions can be employed to modify the release profile, for example, (a) a barrier layer containing the copolymer of the invention can be positioned over a carrier layer containing the copolymer of the invention and a therapeutic agent, (b) multiple carrier layers of the invention, either of the same or different content (e.g., different polymer and/or therapeutic agent content) can be stacked on top of one another, either with or without intervening barrier layers, (c) multiple carrier layers of the invention of differing compositions can be positioned laterally with respect to one another, and so forth. In addition, where a carrier region is employed, a therapeutic-agent concentration gradient can be established within the carrier region to control release of therapeutic agent.

Hence, in certain embodiments of the present invention, the drug release rate of the therapeutic releasing agent is controlled by changing the hydrophilic/hydrophobic ratio of the block copolymer of the present invention such that the overall hydrophilicity of the copolymer is increased or decreased (or, viewed conversely, the overall hydrophobicity is increased or decreased). As will be appreciated by one of skill in the art, the ratio may be changed in a number of ways.

In some aspects, the hydrophilicity of the block copolymer can be increased by forming copolymers with one or more hydrophilic monomers, such as, hydroxyethyl methacrylate or other monomers including those numerous examples of hydrophilic monomers specifically listed above for preparation of high $T_g$ polymer blocks. In alternative embodiments, the hydrophobicity of the resulting copolymer is increased by forming copolymers with one or more hydrophobic monomers. Any one or more of a number of hydrophobic monomers can be used, including but not limited to methyl methacrylate or other monomers including those numerous examples of hydrophobic monomers specifically listed above for preparation of high $T_g$ polymer blocks.

Although one of skill in the art would readily discern whether a monomer is predominantly hydrophilic or hydrophobic, various monomers having hydrophilic or hydrophobic characteristics and which are suitable for use in the present invention and which can be used to modulate the hydrophilic and/or hydrophobic character of the materials of the present invention are exemplified, but not limited, by the following: (1) hydrophobic monomers including the following: vinyl aromatic monomers, including unsubstituted vinyl aromatics, vinyl substituted aromatics, and ring-substituted vinyl aromatics; vinyl esters, vinyl halides, alkyl vinyl ethers, and other vinyl compounds such as 1-vinyl-2-pyrrolidone and vinyl ferrocene; aromatic monomers other than vinyl aromatics, including acenaphthalene and indene; acrylic monomers, including alkyl acrylates, arylalkyl acrylates, alkoxyalkyl acrylates, halo-alkyl acrylates, and cyano-alkyl acrylates; methacrylic monomers, including methacrylic acid esters (methacrylates) and other methacrylic-acid derivatives including methacrylonitrile; acrylic monomers, including acrylic acid esters and other acrylic-acid derivatives including acrylonitrile, alkyl methacrylates and aminoalkyl methacrylates; alkene-based monomers, including ethylene, isotactic propylene, 4-methyl pentene, 1-octadecene, and tetrafluoroethylene and other unsaturated hydrocarbon monomers; cyclic ether monomers; ether monomers other than acrylates and methacrylates; and other monomers including epsilon-caprolactone; and (2) hydrophilic monomers including the following: vinyl amines, alkyl vinyl ethers, and other vinyl compounds; methacrylic monomers including methacrylic acid and methacrylic acid salts; acrylic monomers such as acrylic acid, its anhydride and salt forms, and acrylic acid amides; alkyl vinyl ether monomers such as methyl vinyl ether; and cyclic ether monomers such as ethylene oxide.

In this connection, in some preferred embodiments, the present invention comprises coatings and medical devices having coatings comprising triblock copolymers having endblocks that contain one or more hydrophilic chains, including homopolymer chains of ethylene oxide (PEO), homopolymer chains of vinylpyrrolidone (PVP), or copolymer chains comprising a combination thereof, arranged in a repeating (e.g., alternating), random, statistical or gradient distributions. In other preferred embodiments, the endblocks contain chains comprising one or more hydrophobic polymers such as homopolymer chains of polymethyl methacrylate (PMMA), homopolymer chains of polystyrene, and copolymer chains comprising a combination of the same, arranged in a repeating (e.g., alternating), random, statistical or gradient distribution. The endblocks can also employ a combination of both hydrophilic and hydrophobic monomers that exhibit desired drug diffusion and release properties. The hydrophilic and/or hydrophobic monomers can be selected from various monomer species, including but not limited to those numerous monomers specifically listed above for preparation of high $T_g$ polymer blocks.

In certain embodiments, the drug release rate is controlled by blending hydrophobic or hydrophilic polymers in the release layers of the invention with the copolymers described herein, thereby increasing the hydrophobicity or hydrophilicity, respectively, of the release layers. In one exemplary embodiment, the invention provides a blend comprising a triblock copolymer in accordance with the invention, which is blended with a hydrophilic polymer such as 2-hydroxyethyl methacrylate (HEMA), poly(2-vinyl pyridine) (PVP), or a combination of these materials. The triblock graft copolymer, in a preferred embodiment, comprises a midblock of a polyolefin or polydiene such as EPDM and end blocks of polystyrene copolymer.

As will be appreciated by one of skill in the art, the copolymers of the present invention may be synthesized according to known methods, including ionic and, in particular, radical polymerization methods such as azobis(isobutyronitrile)- or peroxide-initiated processes, and controlled/"living" radical polymerizations such as metal-catalyzed atom transfer radical polymerization (ATRP), stable free-radical polymerization (SFRP), nitroxide-mediated processes (NMP), and degenerative transfer (e.g., reversible addition-fragmentation chain transfer (RAFT)) processes. These methods are well-detailed in the literature and are described, for example, in an article by Pyun and Matyjaszewski, *Synthesis of Nanocomposite Organic/Inorganic Hybrid Materials Using Controlled/"Living" Radical Polymerization*, Chem. Mater., 13:3436-3448 (2001), the contents of which are incorporated by reference in their entirety.

In polymerizations of a monomer (M, in scheme below) via ATRP, radicals are generated by the redox reaction of organic halides such as alkyl halides (RX, in scheme below) with transition-metal complexes ($Met_{+n}$, in scheme below). Radicals can then propagate but are rapidly deactivated by the oxidized form of the transition-metal catalyst. Initiators typically used are α-haloesters (e.g., ethyl 2-boroisobutyrate and methyl 2-bromopropionate) or benzyl halides (e.g., 1-phenylethyl bromide and benzyl bromide). A wide range of transition-metal complexes, such as Ru- (e.g., Grubbs catalyst), Cu-, and Fe-based systems are employed. For Cu-based systems, ligands such as 2,2'-bipyridine and aliphatic amines are typically employed to control both the solubility and activity of various ATRP catalysts. A typical ATRP mechanism is illustrated by the following scheme:

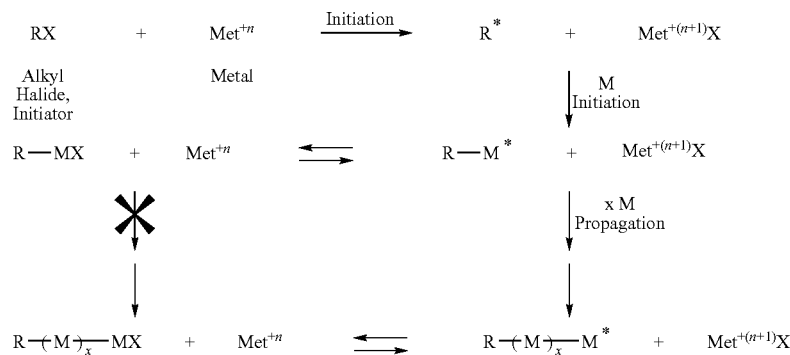

The copolymers of the medical devices of the present invention can be synthesized, for example, by a free radical process that comprises: (a) providing a macro-initiator, the macro-initiator comprising a free radical terminated low $T_g$ block and (b) conducting a free radical polymerization reaction in the presence of a monomer.

In embodiments where it is desirable to synthesize high $T_g$ polymer blocks having a main chain and a plurality of side chains, the polymerization can proceed in the presence of (i) a macro-monomer, which comprises the side chain and has a free-radical polymerizable end group and (ii) a free-radical polymerizable comonomer or a combination of comonomers, each containing a polymerizable unsaturated group. Preferably, the end group is terminally unsaturated and the polymerizable comonomer is an unsaturated monomer.

The polymers of the present invention can also be synthesized using a difunctional free radical initiator such as dimethyl-2,6-heptanedioate, which is used to polymerize, for example, acrylate monomers (e.g., ethyl acrylate) to form a polyacrylate macro-initiator.

A "macro-monomer" as used herein is a macromolecule, commonly a polymer, which has one reactive group, often as an end-group, which enables it to act as a monomer molecule, contributing only a single monomeric unit to a chain of the final macromolecule. Each macromonomer molecule is attached to the main chain of the final polymer by reaction of only one monomeric unit in the macromonomer molecule. Homopolymerization or copolymerization of a macromonomer yields comb or graft polymers. For example, a long-chain vinyl polymer or oligomer (as used herein, an oligomer is a polymer containing from 2-9 constitutional units) that has a polymerizable double bond at the end of the chain is a macromonomer.

Examples of some commonly employed free radical initiator compounds include hydroperoxide, peroxides, such as diacetyl peroxide, di-tert-butyl peroxide, di-benzoyl peroxide, and azo compounds, such as azobis(isobutyronitrile), tertiary butyl perbenzoate, di-cumyl peroxide and potassium persulfate.

Examples of macro-initiators include free radical terminated EPDM. In some embodiments, the macro-initiator is a mono- or di-functional polyolefin compound reacted to yield a 2-bromoisobutyrate end group.

Examples of macro-monomers include polystyrene, polyethylene oxide, polyvinylpyrrolidone, polymethylmethacrylate, each with a polymerizable end group, for example, a group that provides terminal unsaturation, such as alkyl methacrylate-terminated polystyrene.

Examples of comonomers include unsaturated monomers or a combination of monomers, each containing a polymerizable unsaturated group, such as alkyl methacrylates, alkyl acrylates, hydroxyalkyl methacrylates, vinyl esters or styrene.

Example 1

Synthesis of EPDM-Based Block Copolymer

1. Synthesis of EPDM Macroinitiator

A low $T_g$ hydrocarbon polymer block is prepared from EPDM (ethylene-propylene-diene monomer) copolymer blocks (e.g., Vistalon™ polymers from Exxon-Mobil), as described above. The EPDM block copolymer comprises ethylene, propylene and a diene termonomer block, in this case, ethylidene norbornene. End-functional groups are formed on the EPDM by hydroboration of the diene monomers with 9-BBN (9-borabicyclo[3.3.1]nonane), followed by reaction with hydrogen peroxide. Hydroboration of alkenes generally involves attack of the double bond of the ethylidene norbornene monomer by $BH_3$ to form a 4-membered ring transition state (‡), as follows:

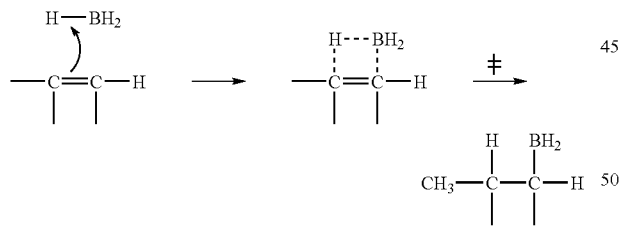

The addition of peroxide resolves the transition state into the alcohol, providing a hydroxyl end-functional group. The hydroxyl groups are then reacted with 2-bromo-isobutyryl bromide to form the EPDM with bromoester end functional groups (EPDM macroinitiator), as shown in FIG. 1.

2. Polystyrene-Poly(EPDM)-Polystyrene Block Copolymer Synthesis

Figure 2:
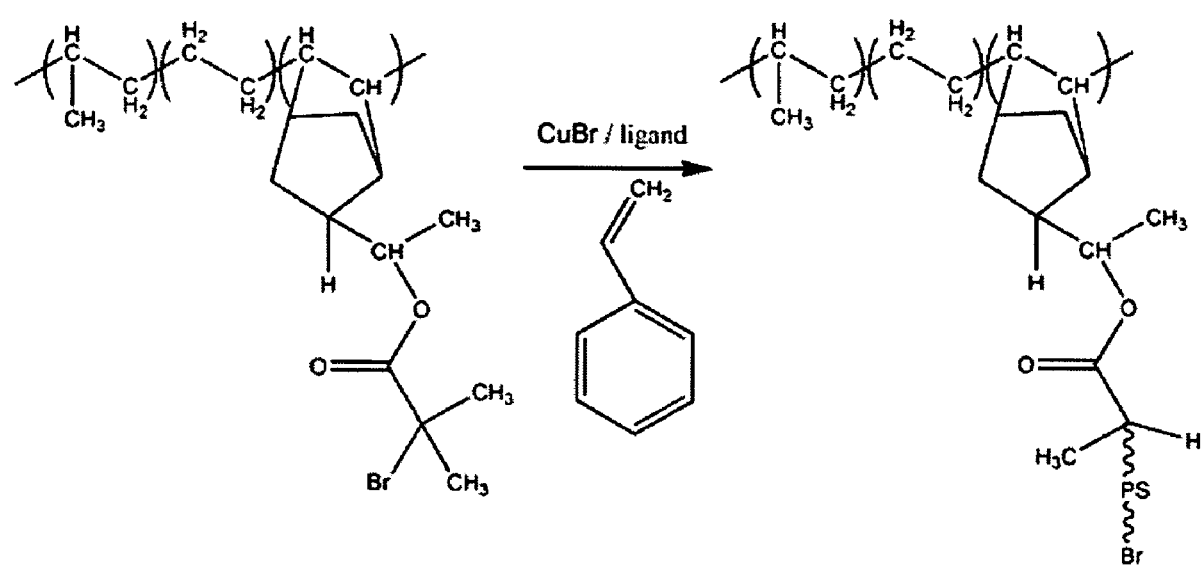
FIG. 2 schematically illustrates the synthesis of a block copolymer having a comb architecture and which comprises poly(EPDM)-graft-polystyrene by the polymerization reaction of the EPDM macroinitiator with styrene monomer under standard controlled/living radical polymerization conditions.

A styrene-EPDM-styrene based block copolymer is synthesized using known techniques, to form an EPDM hydrocarbon backbone with polystyrene side chains. This EPDM macroinitiator is used to polymerize styrene according to published methods for ATRP polymerization. The resulting copolymer comprises a number of polystyrene side chains originating from the double bond in the incorporated norbornene monomer of the EPDM molecule. A representation of a resulting block copolymer having a comb architecture is shown in FIG. 2.

Example 2

Synthesis of Polyolefin-Based Graft Copolymers

A low $T_g$ hydrocarbon polymer block is prepared from functionalized polydiene and polyolefin blocks, such as those which are commercially available with functionalized end groups as poLichelic™ polymers from FMC Lithium (Gastonia, N.C.). For example, the following diol and triols of polyolefins are utilized to formulate the polymeric materials and devices of the present invention.

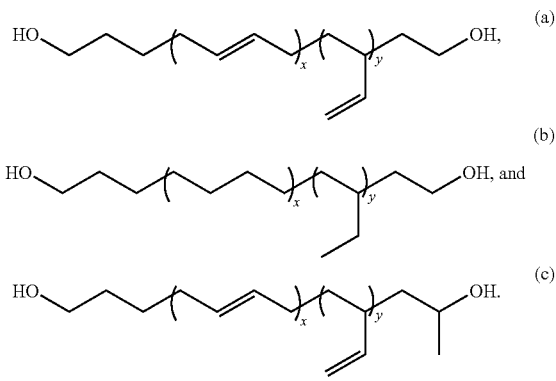

Figure 3:
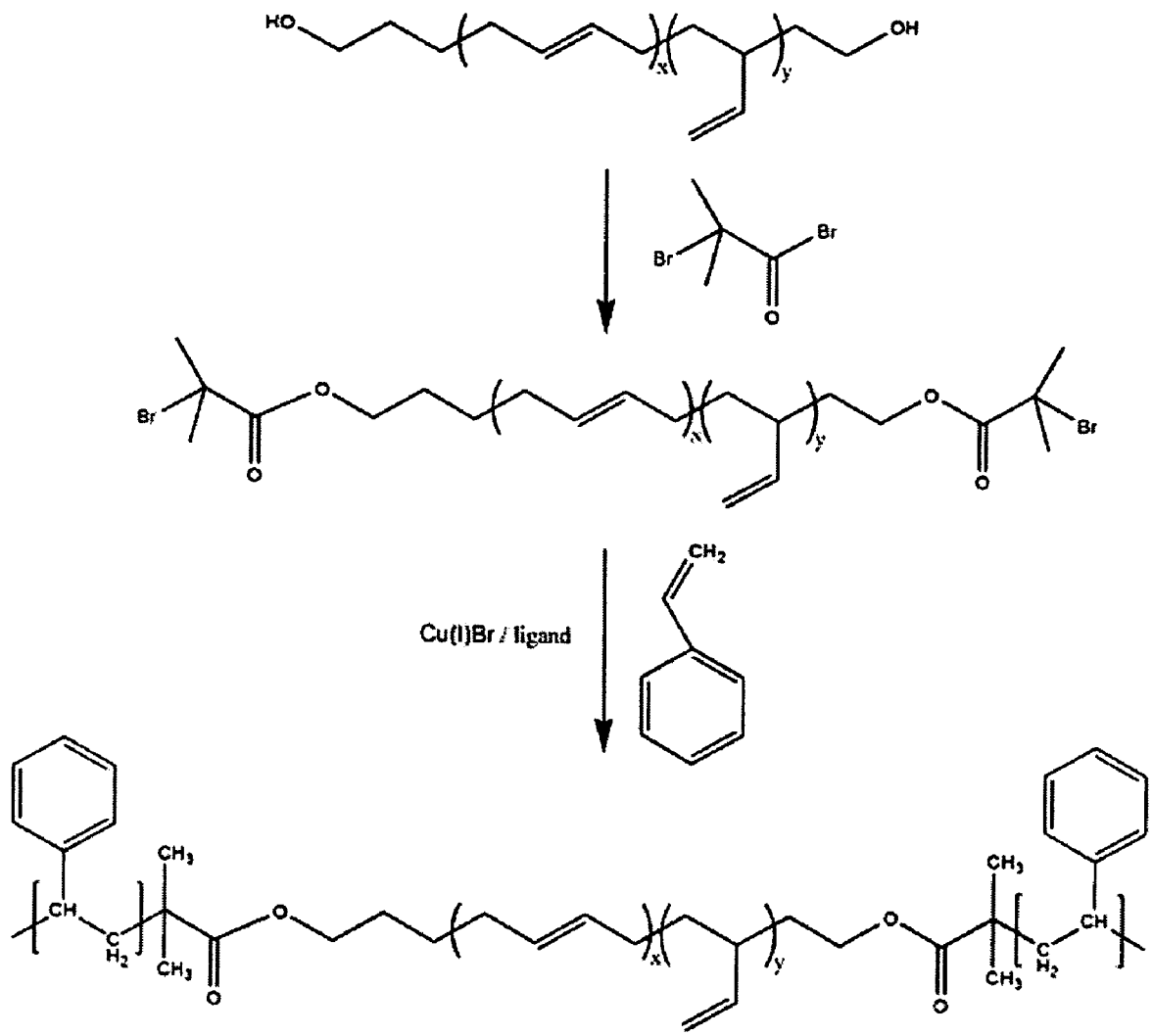
FIGS. 3, 4, and 5 schematically illustrate the synthesis of three triblock copolymers for the medical devices of the present invention comprising polystyrene endblocks and polyolefin midblocks using commercially available telechelic polyolefins.
Figure 4:
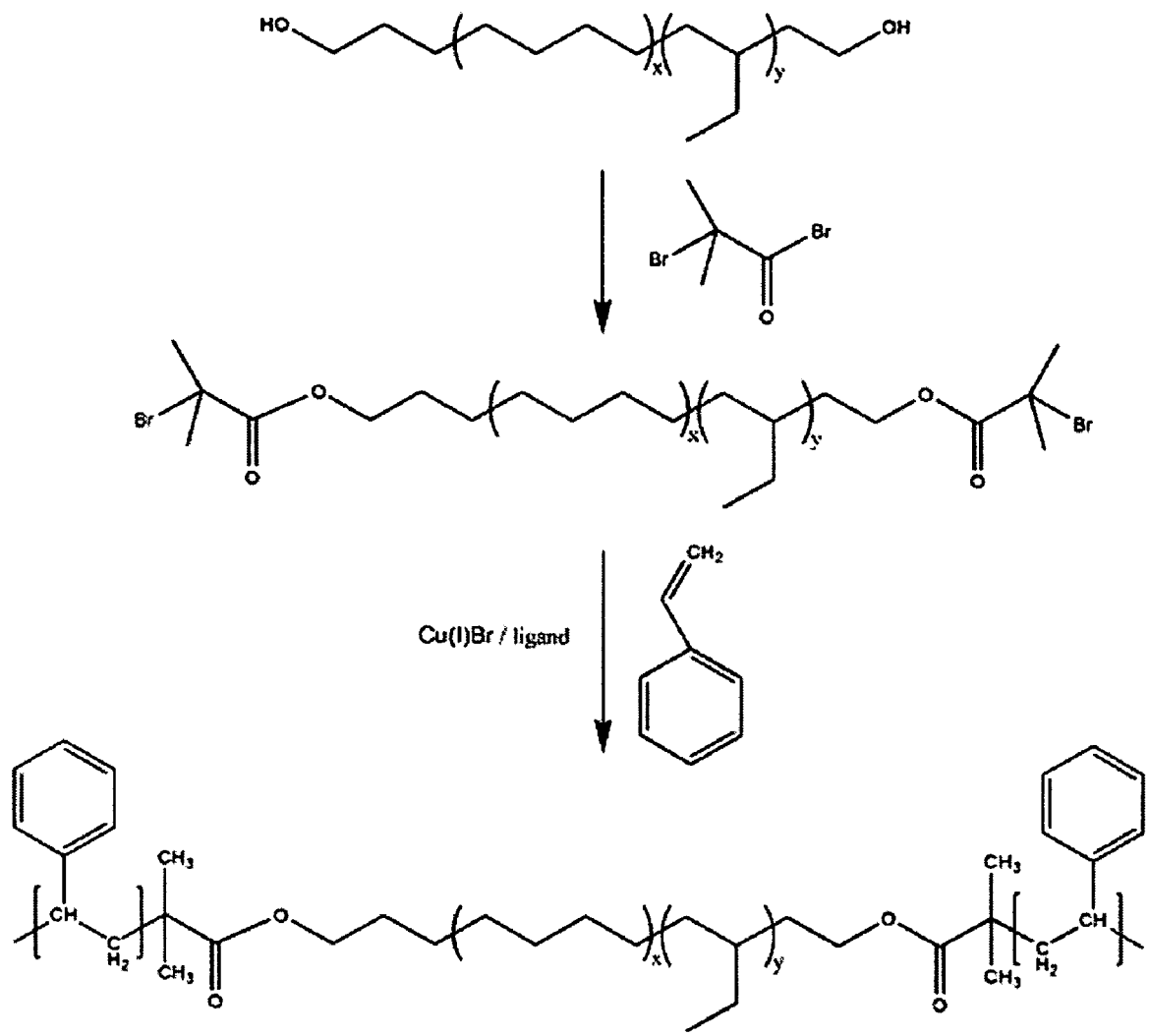
Figure 5:
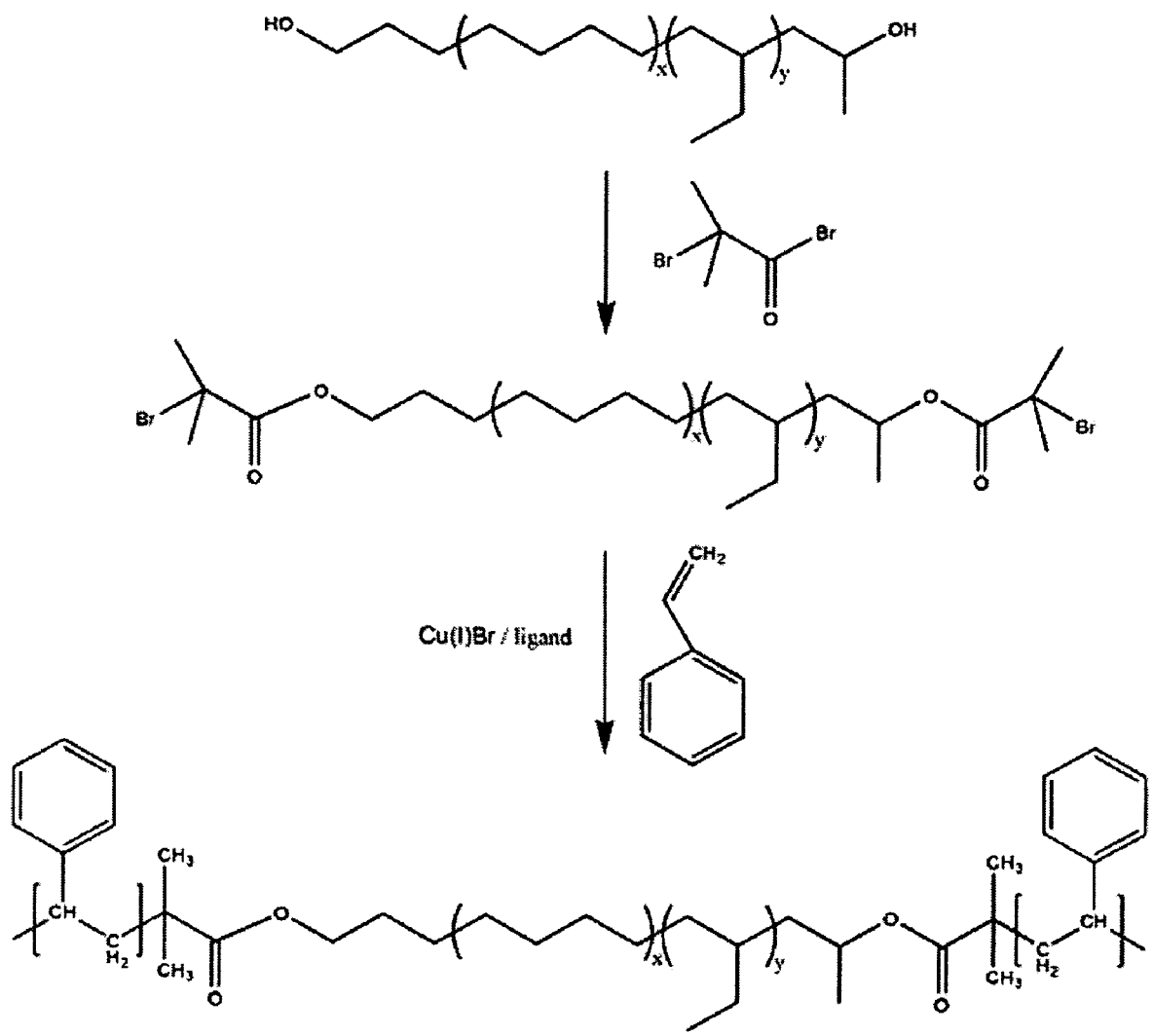

These materials are used in separate experiments to yield linear A-B-A triblock copolymers having a low $T_g$ hydrocarbon midblock and high $T_g$ polymer end blocks such as polystyrene endblocks. A polyolefin copolymer is prepared by first reacting a di-hydroxy-terminated poly(olefin) with 2-bromo-isobutyryl bromide. This forms a macroinitiator with two α-bromoester groups. These groups can be used to initiate the polymerization of styrene to form the triblock copolymer via atom transfer radical polymerization techniques or other controlled/living radical polymerization methods. FIGS. 3, 4, and 5 schematically illustrate the formulation of three linear polystyrene-polyolefin-polystyrene triblock copolymers according to various embodiments of the present invention. These diols and triols, listed above, may also be used to initiate ring opening polymerization of cyclic monomers such as lactide, glycolide, caprolactone, or caprolactam to produce triblock polymers.

Figure 6:
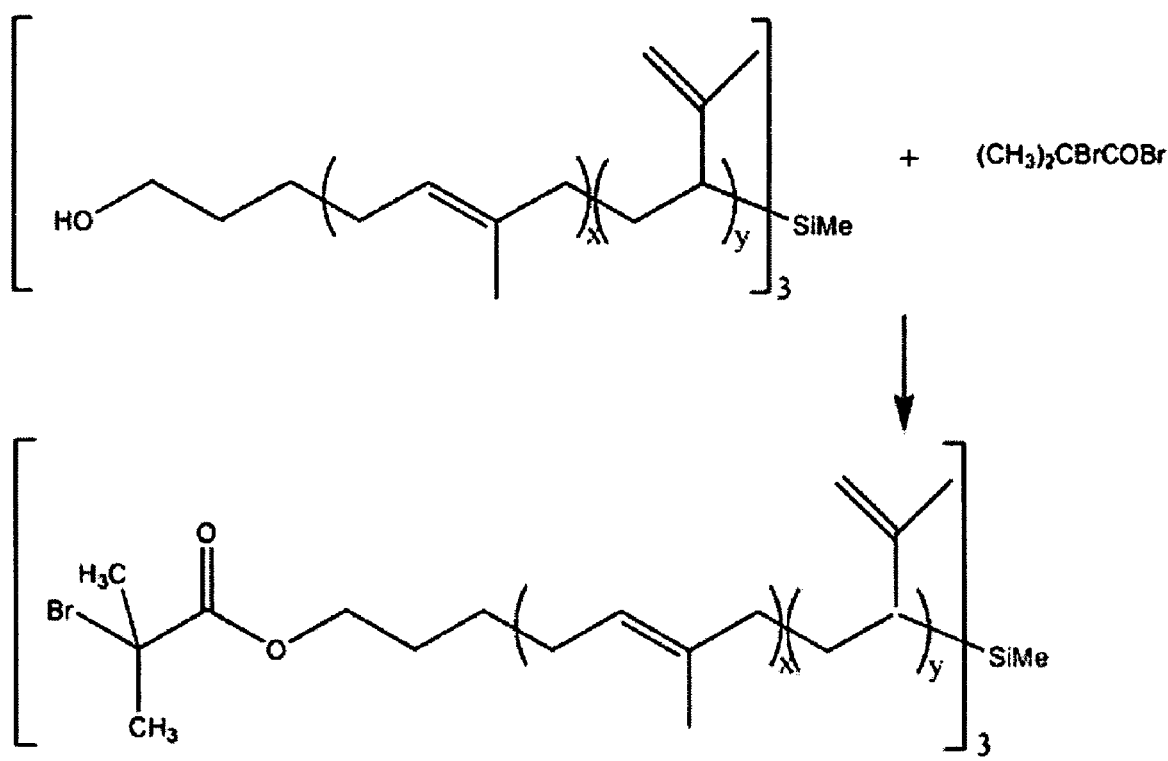
FIG. 6 schematically illustrates the synthesis of a macroinitiator from a hybrid organic/inorganic SiMe polyolefinic molecule having a hydroxyl functional group by reacting the molecule with 2-bromo-isobutyryl bromide to form a α-bromoester end group on the end of the polyolefinic molecule.

In addition, a tri-functional polyolefin having a hybrid inorganic/organic structure is used to create a three-armed star copolymer of the structure, $SiMe-(BA)_3$. The tri-functional SiMe-core polyolefin having a hydroxyl functional group is reacted with 2-bromo-isobutyryl bromide to create a macroinitiator having α-bromoester groups, as schematically illustrated in FIG. 6.

Generally, there are two methods for generating star shaped polymers. One may either link a given number of linear chains to the same central core fitted with reactive functions ("arm first" method) or grow branches from a multifunctional core that is able to initiate the polymerization in multiple directions ("core first" method). The tri-functional SiMe-core polyolefin may be produced according to previously known methods, such as the "arm first" method using commercially available anionic initiators that have protected functional groups (FMC Lithium, Gastonia, N.C.), and are described in U.S. Pat. No. 6,362,284, which is hereby incorporated by reference in its entirety. According to the "arm first" method, a monofunctional hydroxy-protected initiator is used to polymerize typically butadiene or isoprene with, for example, methyltrichlorosilane as a coupling/linking agent. The living polymer chain ends react with silylchloro groups on the methyltrichlorosilane to produce the three arm star polymer. The hydroxy functional groups are formed by the deprotection (hydrolysis) of the protecting group, as described in U.S. Pat. No. 6,362,284.

Figure 7:
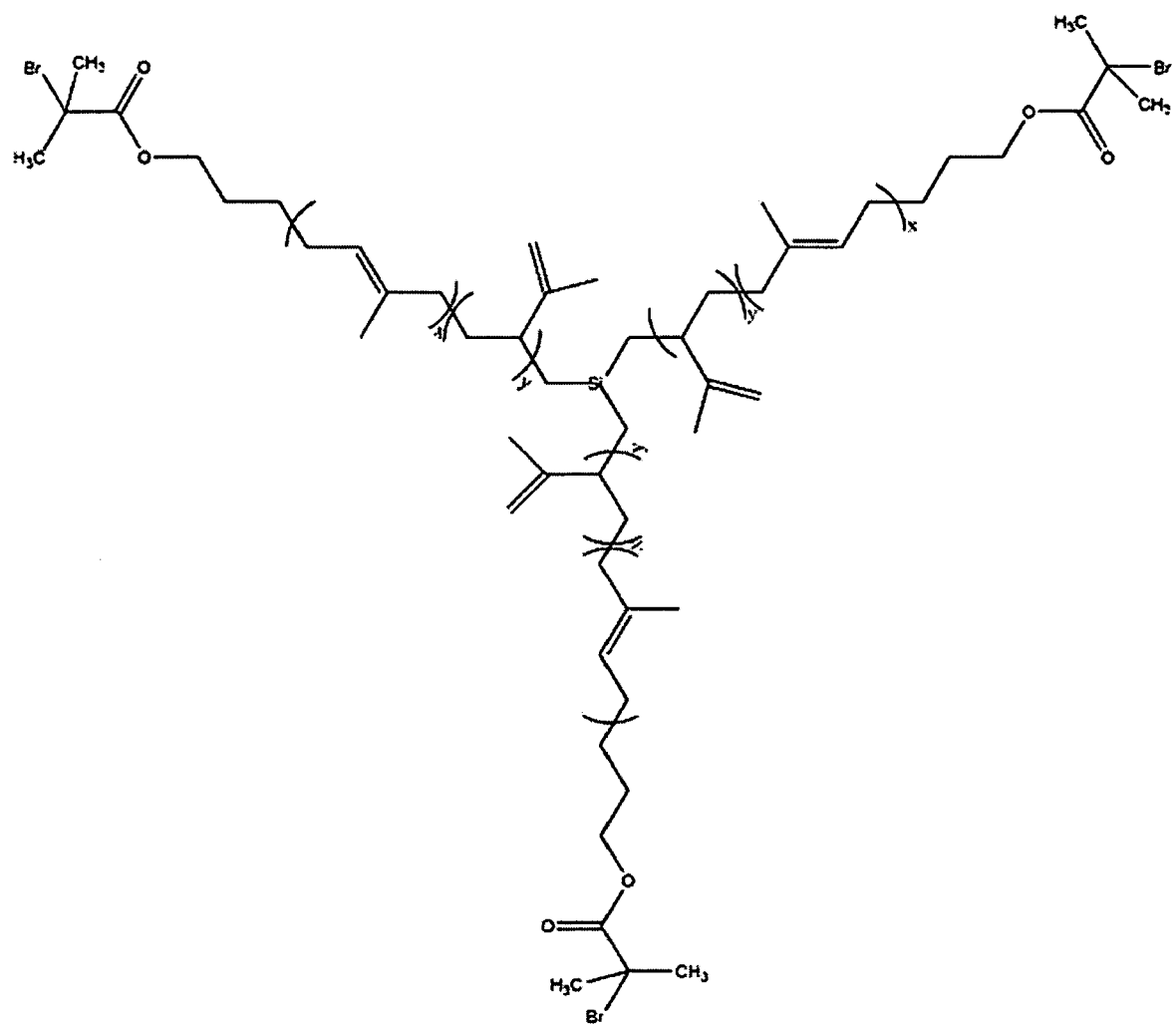
FIG. 7 schematically illustrates the structure of the trifunctional macroinitiator of FIG. 6 from which a three-arm star copolymer can be propagated.
Figure 8:
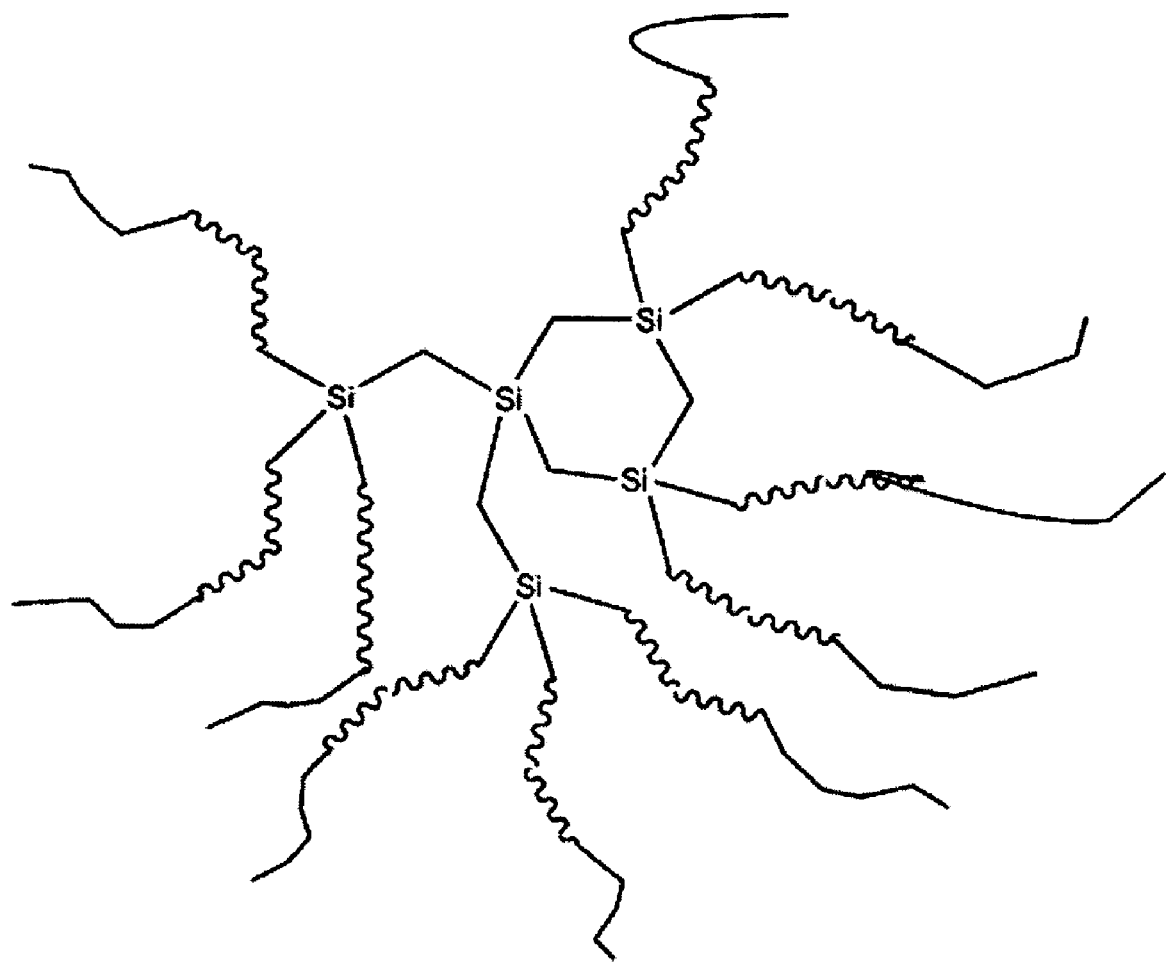
FIG. 8 illustrates an exemplary three-arm star copolymer comprising a tri-functional core (e.g., SiMe core indicated by solid inner lines) with a low $T_g$ hydrocarbon inner chain (e.g., polyolefin indicated by the wavy segments) each connected to a high $T_g$ copolymer outer chain (e.g., polystyrene indicated by the solid outer segments).

As shown in FIG. 7, the macroinitiator comprises a tri-functional SiMe core with polyolefinic arms having reactive end groups comprising α-bromoester groups. The copolymer is formed by polymerizing the macroinitiator with a styrene comonomer under standard atomic transfer radical polymerization conditions. A representative final architecture of a three-arm star comprising a SiMe tri-functional core with polyolefin inner chain lengths connected to polystyrene outer chains, is shown in FIG. 8.

Figure 9:
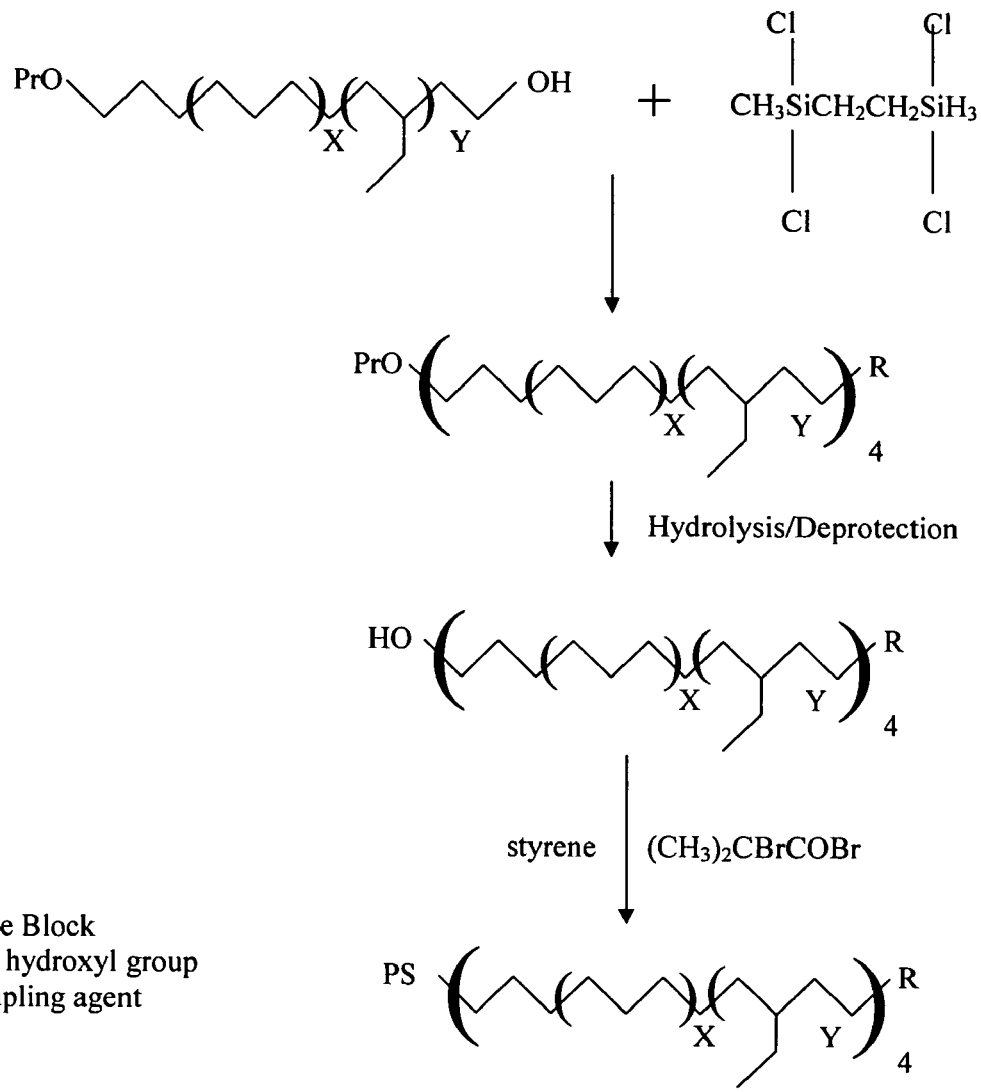
FIG. 9 illustrates an exemplary multi-arm block copolymer produced using a silicone chloride coupling agent. Specifically, a four-arm star polyolefin copolymer comprising two silicone atoms at the core with hydroxy functional end groups is schematically illustrated.

If desired, these hydroxy-protected polyolefin arms, described above, may be coupled with different silicone coupling agent other than methyltrichlorosilane to provide multi-arm block copolymers, as illustrated by FIG. 9. A variety of silicone chloride coupling agents is available through the Gelest Corporation. As shown in FIG. 9, bis(methyldichlorosilyl) ethane may be used as the coupling agent. The living polymer chain ends react with silylchloro groups on the bis(methyldichlorosilyl) ethane to produce a four-arm star polyolefin copolymer with hydroxy functional end groups with the copolymer having two silicone atoms in the center core. As described in U.S. Pat. No. 6,362,284, the hydroxy functional groups are formed by the deprotection (hydrolysis) of the protecting group.

Although various embodiments are specifically illustrated and described herein, it will be appreciated that modifications and variations of the present invention are covered by the above teachings and are within the purview of the appended claims without departing from the spirit and intended scope of the invention.

What is claimed is:

1. A radiation stable medical device comprising (a) a release region and (b) at least one therapeutic agent, said release region comprising a radiation stable copolymer that comprises (i) a low $T_g$ hydrocarbon polymer block and (ii) one or more high $T_g$ polymer blocks, wherein said low $T_g$ hydrocarbon block is a poly(olefin-co-diene) block.

2. The device of claim 1, wherein said copolymer comprises a low $T_g$ hydrocarbon polymer midblock and a plurality of high $T_g$ polymer endblocks.

3. The device of claim 1, wherein said copolymer is a triblock copolymer.

4. The device of claim 1, wherein said copolymer is a star copolymer.

5. The device of claim 1, wherein said copolymer is a dendritic copolymer.

6. The device of claim 1, wherein said copolymer is a comb copolymer comprising a low $T_g$ hydrocarbon polymer main chain and a plurality of high $T_g$ polymer side chains.

7. The device of claim 1, wherein said hydrocarbon block is a poly(olefin-co-diene) block in which the olefin comprises one or both of ethylene and propylene and the diene comprises vinyl norbornene or ethylidene norbornene.

8. The device of claim 1, wherein said high $T_g$ block is selected from the group consisting of a poly (vinyl aromatic) block, a poly(alkyl methacrylate) block and a poly(vinyl pyridine) block.

9. The device of claim 1, wherein said high $T_g$ block comprises polystyrene.

10. The device of claim 1, wherein said release region is a carrier region that comprises said therapeutic agent.

11. The device of claim 1, wherein said release region is a barrier region disposed over a therapeutic-agent-containing region that comprises said therapeutic agent.

12. The device of claim 1, wherein said release region is in the form of a coating layer that covers all or a part of said medical device.

13. The device of claim 1, wherein said medical device is an implantable or insertable medical device.

14. The device of claim 1, wherein said implantable or insertable medical device is selected from a catheter, a guide wire, a balloon, a filter, a stent, a stent graft, a vascular graft, a vascular patch and a shunt.

15. The device of claim 1, wherein said implantable or insertable medical device is adapted for implantation or insertion into the coronary vasculature, peripheral vascular system, esophagus, trachea, colon, biliary tract, urinary tract, prostate or brain.

16. The device of claim 1, wherein said therapeutic agent is selected from one or more of the group consisting of anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

17. The device of claim 2, wherein said copolymer is made by a process that comprises (a) providing a macro-initiator, said macro-initiator comprising a free radical terminated low $T_g$ hydrocarbon block and (b) conducting a free radical polymerization reaction in the presence of a macro-monomer comprising said endblocks each having a free-radical polymerizable end group.

18. The device of claim 17, wherein the macro-monomer comprises a polystyrene block, a polyethylene oxide block, a polyvinylpyrrolidone block, a polyalkylmethacrylate block, or a combination thereof.

19. The device of claim 17, wherein the macro-initiator is a free radical terminated (ethylene-propylene-diene monomer) copolymer block.

20. The device of claim 17, wherein the free radical polymerization reaction is further conducted in the presence of one or more hydrophilic monomers selected from vinyl amine monomers, alkyl vinyl ether monomers, methacrylic acid and acid salt monomers, acrylic acid monomer, acrylic acid amide monomers, alkyl vinyl ether monomers, cyclic ether monomers, or one or more hydrophobic monomers selected from vinyl aromatic monomers, vinyl ester monomers, vinyl halide monomers, alkyl vinyl ether monomers, 1-vinyl-2-pyrrolidone monomer, vinyl ferrocene monomer, acenaphthalene monomer, indene monomer, alkyl acrylate monomers, arylalkyl acrylate monomers, alkoxyalkyl acrylate monomers, halo-alkyl acrylate monomers, cyano-alkyl acrylate monomers, alkyl methacrylate monomers, aminoalkyl methacrylate monomers, methacrylonitrile monomer, acrylonitrile monomer, ethylene monomer, isotactic propylene monomer, 4-methyl pentene monomer, 1-octadecene monomer, tetrafluoroethylene monomer, cyclic ether monomers, ether monomers, and epsilon-caprolactone monomer.

21. A method of forming the medical device of claim 1, comprising: (a) providing a solution comprising (i) a solvent system and (ii) said copolymer; and (b) forming said release region from said solution by removing said solvent system from said solution.

22. The method of claim 21, wherein said solution further comprises a therapeutic agent in dissolved or dispersed form.

23. The method of claim 21, wherein said solution is applied over a therapeutic-agent-containing region that comprises said therapeutic agent.

24. The method of claim 21, wherein said release region is formed by a technique comprising a spraying process.

25. The device of claim 1, wherein the olefin monomer in said poly(olefin-co-diene) block comprises ethylene and propylene.

26. The device of claim 25, wherein the diene monomer in said poly(olefin-co-diene) block comprises a cyclic diolefin having from about 6 to about 15 carbon atoms.

27. The device of claim 1, wherein the diene monomer in said poly(olefin-co-diene) block comprises a cyclic diolefin having from about 6 to about 15 carbon atoms.

28. The device of claim 1, wherein the diene monomer in said poly(olefin-co-diene) block comprises a cyclic diolefin selected from 1,3-cyclopentadiene, tetrahydroindene, dicyclopentadiene, vinyl norbornene, ethylidene norbornene 5-methylene-2-norbornene, 5-ethylidene-2-norbornene, 5-isopropylidene-2-norbornene, 5-(4-cyclopentenyl)-2-norbornene, 5-cyclohexylidene-2-norbornene, 5-vinyl-2-cyclododecene, allyl cyclohexene, vinyl cyclooctene, allyl cyclodecene, and vinyl cyclododecene.

29. The device of claim 27, wherein the olefin monomer in said poly(olefin-co-diene) block comprises a monomer selected from ethylene, propylene, 1-butene, 1-pentene, 1-hexene, 1-octene, 1-decene, cyclobutene, cyclopentene, norbornene, alkyl substituted norbornene, and combinations thereof.

30. The device of claim 27, wherein the wherein said high $T_g$ block is a poly (vinyl aromatic) block.

31. The device of claim 27, wherein the wherein said high $T_g$ block is a poly(alkyl methacrylate) block.

32. The device of claim 27, wherein the wherein said high $T_g$ block is a poly(vinyl pyridine) block.

* * * * *